United States Patent
Zeiner et al.

(10) Patent No.: US 9,074,203 B2
(45) Date of Patent: Jul. 7, 2015

(54) LIGATION METHOD EMPLOYING RTCB

(75) Inventors: Gusti Zeiner, San Mateo, CA (US); Robert A. Ach, San Francisco, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 313 days.

(21) Appl. No.: 13/368,600

(22) Filed: Feb. 8, 2012

(65) Prior Publication Data

US 2012/0208707 A1    Aug. 16, 2012

Related U.S. Application Data

(60) Provisional application No. 61/441,589, filed on Feb. 10, 2011.

(51) Int. Cl.
| | |
|---|---|
| *C12P 21/04* | (2006.01) |
| *C12N 15/10* | (2006.01) |
| *C12N 15/66* | (2006.01) |
| *C12N 9/00* | (2006.01) |
| *C12P 19/34* | (2006.01) |

(52) U.S. Cl.
CPC ............... *C12N 15/10* (2013.01); *C12N 15/66* (2013.01); *C12N 9/93* (2013.01); *C12Y 605/01004* (2013.01); *C12P 19/34* (2013.01)

(58) Field of Classification Search
None
See application file for complete search history.

(56) References Cited

PUBLICATIONS

Englert, et al., "Archaeal 3'-phosphate RNA splicing ligase characterization identifies the missing component in tRNA maturation", Proc Natl Acad Sci, 2011, 108:1290-5.
Genschik, et al., "The human RNA 3'-terminal phosphate cyclase is a member of a new family of proteins conserved in Eucarya, Bacteria and Archaea", EMBO J, 1997, 16:2955-67.
Okada, et al., "Crystal structure of an RtcB homolog protein (PH1602-extein protein) from *Pyrococcus horikoshii* reveals a novel fold", Proteins, 2006, 63:1119-22.
Tanaka, et al., "RtcB, a novel RNA ligase, can catalyze tRNA splicing and HAC1 mRNA splicing in vivo", J Biol Chem, 2011, 286:30253-7.
Tanaka, et al., "RtcB is the RNA ligase component of an *Escherichia coli* RNA repair operon", J Biol Chem, 2011, 286:7727-31.
Torchia, et al, "Archaeal RNA ligase is a homodimeric protein that catalyzes intramolecular ligation of single-stranded RNA and DNA", Nucleic Acids, 2008, 36:6218-27.

*Primary Examiner* — Michele K Joike

(57) ABSTRACT

A method of processing an RNA sample is provided. In certain embodiments, the method may comprise: a) obtaining a fragmented RNA sample comprising: i. RNA fragments of long RNA molecules; and ii. unfragmented short RNA; and b) contacting said fragmented RNA sample with a first adaptor in the presence of a RtcB ligase, thereby producing a ligated RNA sample comprising adaptor-ligated fragments of long RNA. A kit for performing the method is also provided.

19 Claims, 1 Drawing Sheet

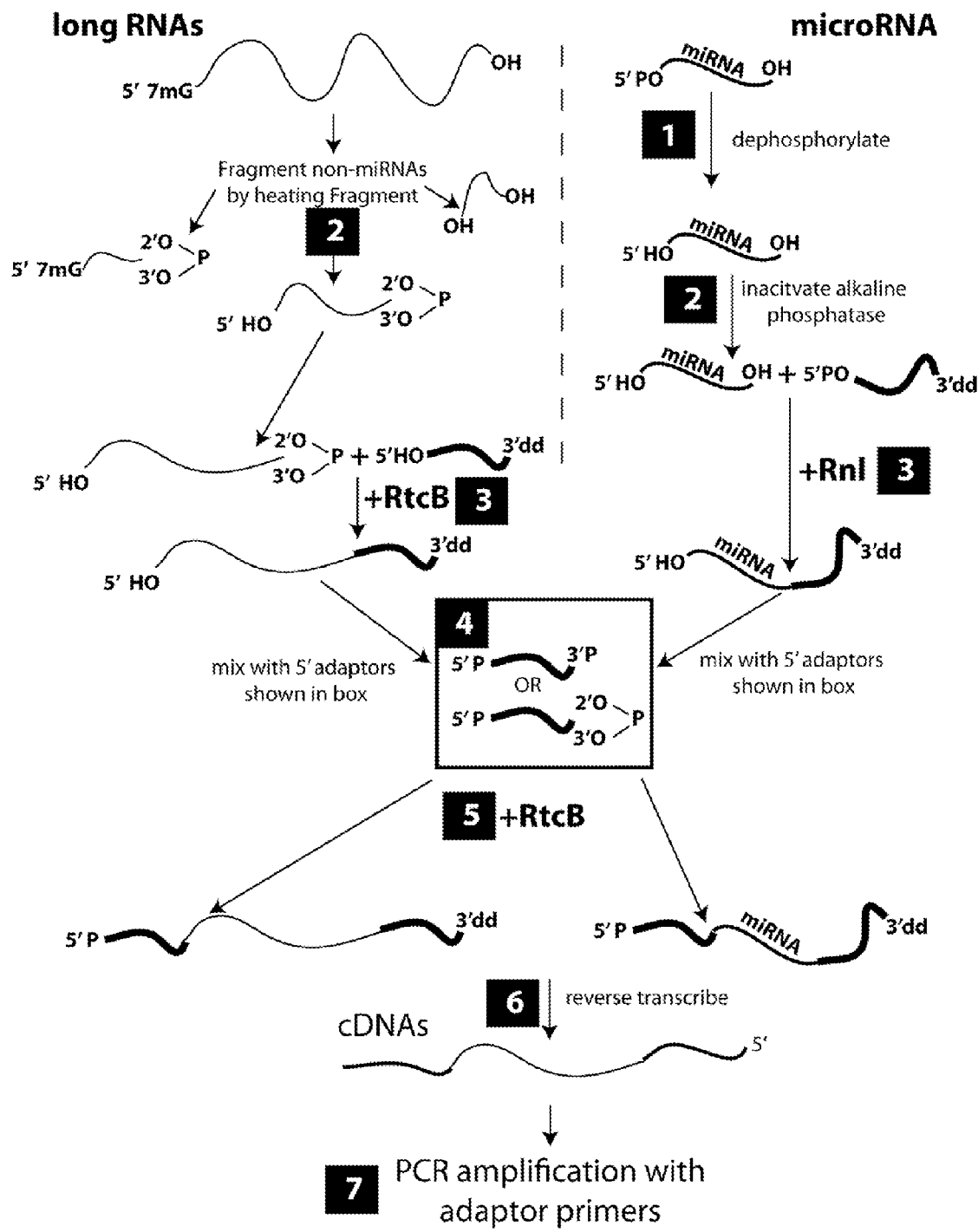

LIGATION METHOD EMPLOYING RTCB

CROSS-REFERENCING

This patent application claims the benefit of U.S. provisional application Ser. No. 61/441,589, filed on Feb. 10, 2011, which application is incorporated by reference herein in its entirety.

INTRODUCTION

Total RNA samples typically contain RNA molecules that vary in length. For example, a typical total RNA sample obtained from mammalian cells may contain mRNA molecules (which generally range in size from a few hundred bases to several kb), lincRNA molecules (which are classified as being at least 200 bases in length), 18S and 28S rRNA molecules (which are approximately 1.9 kb and 5 kb, respectively), tRNA molecules (which are generally below 100 nt in length), and a variety of small RNA molecules (e.g., short interfering RNAs, microRNAs, tiny non-coding RNAs, small modulators RNAs and piwi-interacting RNAs) some of which are in the range of 18 to 25 bases in length.

SUMMARY

A method of processing an RNA sample is provided. In certain embodiments, the method may comprise: a) obtaining a fragmented RNA sample comprising: i. RNA fragments of long RNA molecules; and ii. unfragmented short RNA; and b) contacting said fragmented RNA sample with a first adaptor in the presence of a RtcB ligase, thereby producing a ligated RNA sample comprising adaptor-ligated fragments of long RNA. A kit for performing the method is also provided.

Once made, the ligated RNA sample may be employed in a variety of different protocols. For example, another adaptor can be ligated to the other end of the adaptor-ligated fragments and the fragments can be amplified. Alternatively, the fragments can be used to make a sequencing library. In one exemplary embodiment, the adaptor may comprise an affinity tag, and the method may further comprise separating the adaptor-ligated fragments of long RNA from said non-ligated short RNAs using the affinity tag.

As will be described in greater detail below, the method may optionally include ligating the unfragmented short RNA molecules to a second adaptor using a ligase that recognizes a 3'-OH. In these embodiments, the ligated RNA sample contains both adaptor-ligated fragments of long RNA and adaptor-ligated short RNAs. In the following description and unless indicated otherwise, reference to "a ligated RNA sample" is intended to refer to either: a) a sample that contains only adaptor-ligated fragments of long RNA or b) a sample that contains adaptor-ligated fragments of long RNA and adaptor-ligated short RNAs.

In certain embodiments, the fragmented RNA sample may be made by exposing an initial RNA sample comprising intact long RNA molecules and unfragmented short RNA molecules to fragmentation conditions that favor fragmentation of the long RNA molecules relative to the short RNAs molecules. In particular cases, the exposing may comprise contacting the initial RNA sample with a divalent cation at a temperature of at least 50° C., although other methods are known.

In some embodiments, the unfragmented short RNA molecules may be processed by contacting an initial RNA sample comprising small RNA molecules having a 5'-phosphate and a 3'-OH with an enzyme, e.g., a phosphatase, that removes the 5'-phosphate from the short RNA molecules.

In certain embodiments the method may further comprise contacting the fragmented RNA sample with a second adaptor comprising a 5'-phosphate and a blocked 3' end in the presence of a 3'-OH-dependent single-stranded RNA ligase, thereby producing a ligated RNA sample comprising, in addition to the adaptor-ligated fragments of long RNA, adaptor-ligated short RNA molecules comprising a 5'-OH and a blocked 3' end.

The RNA product may in certain cases be reverse transcribed using a primer that binds to the 5' ends of the first and second adaptors to produce a plurality of cDNA products. The primer may, in certain cases, comprise unstructured nucleic acid (UNA) nucleotides. The cDNA products may be clonally amplified and sequenced using, for example, a so called next generation sequencing method. Alternatively, the cDNA may be amplified and/or labeled and analyzed in some other way, e.g., by hybridizing it to a microarray.

In alternative embodiments, the method may include contacting the ligated RNA sample, which may contain RNAs having a 5'-OH and a blocked 3', regardless of which adaptor participated in the initial ligation, with an independent third adaptor comprising a blocked 5' end (i.e., blocked in that RtcB cannot use it as a substrate, such as 5'P) and a 2'OH, 3' phosphate or 2',3'-cyclic phosphate in the presence of an RtcB ligase, thereby producing a population of RNAs comprising i. the third adaptor at the 5' end and ii. either the first adaptor or second adaptor at the 3' end. In these embodiments, the method may further comprise reverse transcribing the population of RNAs using a primer that can bind to the first and second adaptors to produce a plurality of cDNA products. In some cases, these cDNA products may be clonally amplified and sequenced, as described above. Alternatively, the cDNA may be amplified and/or labeled and analyzed in some other way, e.g., by hybridizing it to a microarray.

In a particular embodiment, the first and second adaptors have different sequences, and the method further comprises amplifying either the adaptor-ligated fragments of long RNA or the adaptor-ligated short RNA using a first primer that is complementary to only one of said first and second adaptors or its complement and a second primer that is complementary to said third adaptor or its complement.

Alternatively, the first and second adaptors have the same sequence, and the method further comprises amplifying both the adaptor-ligated fragments of long RNA and the adaptor-ligated short RNA using a first primer that is complementary to both of said first and second adaptors or their complement and a second primer that is complementary to said third adaptor or its complement. RtcB has been identified in a variety of thermotolerant species as well as mesophilic species and, as such, in certain cases the RtcB ligase used in the method may be heat stable or not. In one embodiment, an RtcB ligase used in the method has an amino acid sequence that is at least 80% identical to a wild-type enzyme sequence, several of which are known (Englert 2011 PNAS). In particular cases, the enzymes may have an amino acid sequence that is at least 80% identical to wild-type enzymes from heat-tolerant archaebacterium, for example.

A kit for performing the method is also provided. In certain embodiments, the kit may comprise any combination of reagents described above, including, e.g.: a) a RtcB ligase which may in certain cases be thermostable; b) a phosphatase that removes the 5'-phosphate of a nucleic acid; and c) an adaptor that comprises a 5'-OH and a blocked 3' end. The kit may optionally contain other components, for example: reagents for fragmenting an RNA sample, a second adaptor that comprises a 5'-phosphate and a 3'-dideoxy group, a third adaptor that contains a 5'-phosphate and a 2'OH, 3'-phosphate or 2',3'-cyclic phosphate, a 3'-OH-dependent single-stranded RNA ligase (which may also be thermostable) and/or a reverse transcriptase.

BRIEF DESCRIPTION OF THE FIGURES

FIG. 1 schematically illustrates a method by which a total RNA library suitable for high throughput sequencing may be generated.

DEFINITIONS

The term "RNA sample", as used herein, relates to a mixture of materials, typically, although not necessarily, in liquid form, containing one or more RNA molecules. An RNA sample may be obtained from cells, e.g., mammalian cells, for example. An RNA sample may contain a population of different RNA molecules, in which case it may contain more than 1,000, more than 10,000, more than 50,000, or more than 100,000 up to 1M or more different species of RNA, i.e., RNA molecules of different sequence.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated purines or pyrimidines, halogenated purines or pyrimidines, deaza-purines or pyrimidines or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, are functionalized as ethers, amines, such as but not limited to MOE, LNA or the likes. Nucleotides may include those that when incorporated into an extending strand of a nucleic acid enables continued extension (non-chain terminating nucleotides) and those that prevent subsequent extension (e.g. chain terminators).

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally occurring nucleotides include guanine, cytosine, adenine, thymine and uridine (G, C, A T and U, respectively).

The terms "ribonucleic acid" and "RNA" as used herein mean a polymer composed of ribonucleotides.

The terms "deoxyribonucleic acid" and "DNA" as used herein mean a polymer composed of deoxyribonucleotides.

"Isolated" or "purified" generally refers to isolation of a substance (compound, polynucleotide, protein, polypeptide, polypeptide composition) such that the substance comprises a significant percent (e.g., greater than 1%, greater than 2%, greater than 5%, greater than 10%, greater than 20%, greater than 50%, or more, usually up to about 90%-100%) of the sample in which it resides. In certain embodiments, a substantially purified component comprises at least 50%, 80%-85%, or 90-95% of the sample. Techniques for purifying polynucleotides and polypeptides of interest are well-known in the art and include, for example, ion-exchange chromatography, affinity chromatography and sedimentation according to density. Generally, a substance is purified when it exists in a sample in an amount, relative to other components of the sample, that is not found naturally.

The term "oligonucleotide", as used herein, denotes a single-stranded multimer of nucleotides from about 2 to 500 nucleotides, e.g., 2 to 200 nucleotides. Oligonucleotides may be synthetic or may be made enzymatically, and, in some embodiments, are 4 to 50 nucleotides in length. Oligonucleotides may contain ribonucleotide monomers (i.e., may be RNA oligonucleotides) or deoxyribonucleotide monomers, or both ribonucleotide monomers and deoxyribonucleotide monomers and may additionally comprise non-natural or modified nucleotide monomers. Oligonucleotides may be 5 to 20, 11 to 30, 31 to 40, 41 to 50, 51-60, 61 to 70, 71 to 80, 80 to 100, 100 to 150 or 150 to 200, up to 500 nucleotides in length, for example. An oligonucleotide may be labeled or unlabeled.

The term "label", as used herein, in the context of a labeled oligonucleotide (e.g., a labeled adaptor) refers to moiety via which an oligonucleotide can be detected or purified. Mass tags, fluorescent tags, chemiluminescent tags and affinity tags (e.g., biotin), are examples of labels.

The term "duplex" or "double-stranded" as used herein refers to nucleic acids formed by hybridization of two single strands of nucleic acids containing complementary sequences. In most cases, genomic DNA is double-stranded.

The term "complementary" as used herein refers to a nucleotide sequence that base-pairs by non-covalent bonds to a target nucleic acid of interest. In the canonical Watson-Crick base pairing, adenine (A) forms a base pair with thymine (T), as does guanine (G) with cytosine (C) in DNA. In RNA, thymine is replaced by uracil (U). As such, A is complementary to T and G is complementary to C. In RNA, A is complementary to U and vice versa. Typically, "complementary" refers to a nucleotide sequence that is at least partially complementary. The term "complementary" may also encompass duplexes that are fully complementary such that every nucleotide in one strand is complementary to every nucleotide in the other strand in corresponding positions. In certain cases, a nucleotide sequence may be partially complementary to a target, in which not all nucleotide is complementary to every nucleotide in the target nucleic acid in all the corresponding positions.

The term "probe," as used herein, refers to a nucleic acid that is complementary to a nucleotide sequence of interest. In certain cases, detection of a target analyte requires hybridization of a probe to the target. In certain embodiments, a probe may be surface-tethered, i.e., immobilized on a surface of a substrate, where the substrate can have a variety of configurations, e.g., a sheet, bead, or other structure. In certain embodiments, a probe may be present on a surface of a planar support, e.g., in the form of an array.

The phrase "surface-bound nucleic acid" refers to a nucleic acid that is immobilized on a surface of a solid substrate, where the substrate can have a variety of configurations, e.g., a sheet, bead, or other structure. In certain embodiments, the nucleic acid probes employed herein are present on a surface of the same planar support, e.g., in the form of an array.

The phrase "labeled population of nucleic acids" refers to mixture of nucleic acids that are detectably labeled, e.g., fluorescently labeled or labeled with other detectable molecular tags, such that the presence of the nucleic acids can be detected by assessing the presence of the label.

The term "array" encompasses the term "microarray" and refers to an ordered array presented for binding to nucleic acids and the like.

An "array," includes any two-dimensional or three-dimensional arrangement of addressable regions, e.g., spatially addressable regions or optically addressable regions, bearing nucleic acids, particularly oligonucleotides or synthetic mimetics thereof, and the like. In some cases, the addressable regions of the array may not be physically connected to one another, for example, a plurality of beads that are distinguishable by optical or other means may constitute an array. Where the arrays are arrays of nucleic acids, the nucleic acids may be adsorbed, physisorbed, chemisorbed, or covalently attached to the arrays at any point or points along the nucleic acid chain.

Any given substrate may carry one, two, four or more arrays disposed on a surface of the substrate. Depending upon the use, any or all of the arrays may be the same or different from one another and each may contain multiple spots or features. An array may contain one or more, including more than two, more than ten, more than one hundred, more than one thousand, more than ten thousand features, or even more than one hundred thousand features, in an area of less than 20 cm$^2$ or even less than 10 cm$^2$, e.g., less than about 5 cm$^2$, including less than about 1 cm$^2$, less than about 1 mm$^2$, e.g., 100 µm$^2$, or even smaller. For example, features may have widths (that is, diameter, for a round spot) in the range from a 5 µm to 1.0 cm. In other embodiments each feature may have a width in the range of 1.0 µm to 1.0 mm, usually 5.0 µm to 500 µm, and more usually 10 µm to 200 µm. Non-round features may have area ranges equivalent to that of circular features with the foregoing width (diameter) ranges. At least some, or all, of the features are of different compositions (for example, when any repeats of each feature composition are excluded the remaining features may account for at least 5%, 10%, 20%, 50%, 95%, 99% or 100% of the total number of features). Inter-feature areas will typically (but not essentially) be present which do not carry any nucleic acids (or other biopolymer or chemical moiety of a type of which the features are composed). Such inter-feature areas typically will be present where the arrays are formed by processes involving drop deposition of reagents but may not be present when, for example, photolithographic array fabrication processes are used. It will be appreciated though, that the inter-feature areas, when present, could be of various sizes and configurations.

Each array may cover an area of less than 200 cm$^2$, or even less than 50 cm$^2$, 5 cm$^2$, 1 cm$^2$, 0.5 cm$^2$, or 0.1 cm$^2$. In certain embodiments, the substrate carrying the one or more arrays will be shaped generally as a rectangular solid (although other shapes are possible), having a length of more than 4 mm and less than 150 mm, usually more than 4 mm and less than 80 mm, more usually less than 20 mm; a width of more than 4 mm and less than 150 mm, usually less than 80 mm and more usually less than 20 mm; and a thickness of more than 0.01 mm and less than 5.0 mm, usually more than 0.1 mm and less than 2 mm and more usually more than 0.2 mm and less than 1.5 mm, such as more than about 0.8 mm and less than about 1.2 mm.

Arrays can be fabricated using drop deposition from pulsejets of either precursor units (such as nucleotide or amino acid monomers) in the case of in situ fabrication, or the previously obtained nucleic acid. Such methods are described in detail in, for example, the previously cited references including U.S. Pat. No. 6,242,266, U.S. Pat. No. 6,232,072, U.S. Pat. No. 6,180,351, U.S. Pat. No. 6,171,797, U.S. Pat. No. 6,323,043, U.S. Patent Application Publication No. 20040203138 by Caren et al., and the references cited therein. As already mentioned, these references are incorporated herein by reference. Other drop deposition methods can be used for fabrication, as previously described herein. Also, instead of drop deposition methods, photolithographic array fabrication methods may be used. Inter-feature areas need not be present particularly when the arrays are made by photolithographic methods as described in those patents.

Arrays may also be made by distributing pre-synthesized nucleic acids linked to beads, also termed microspheres, onto a solid support. In certain embodiments, unique optical signatures are incorporated into the beads, e.g. fluorescent dyes, that could be used to identify the chemical functionality on any particular bead. Since the beads are first coded with an optical signature, the array may be decoded later, such that correlation of the location of an individual site on the array with the probe at that particular site may be made after the array has been made. Such methods are described in detail in, for example, U.S. Pat. Nos. 6,355,431, 7,033,754, and 7,060,431.

An array is "addressable" when it has multiple regions of different moieties (e.g., different oligonucleotide sequences) such that a region (i.e., a "feature" or "spot" of the array) at a particular predetermined location (i.e., an "address") on the array contains a particular sequence. Array features are typically, but need not be, separated by intervening spaces. An array is also "addressable" if the features of the array each have an optically detectable signature that identifies the moiety present at that feature. An array is also "addressable" if the features of the array each have a signature, which is detectable by non-optical means, that identifies the moiety present at that feature.

The terms "determining", "measuring", "evaluating", "assessing", "analyzing", and "assaying" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

The term "using" has its conventional meaning, and, as such, means employing, e.g., putting into service, a method or composition to attain an end. For example, if a program is used to create a file, a program is executed to make a file, the file usually being the output of the program. In another example, if a computer file is used, it is usually accessed, read, and the information stored in the file employed to attain an end. Similarly if a unique identifier, e.g., a barcode is used, the unique identifier is usually read to identify, for example, an object or file associated with the unique identifier.

As used herein, the term "$T_m$" refers to the melting temperature of an oligonucleotide duplex at which half of the duplexes remain hybridized and half of the duplexes dissociate into single strands. The $T_m$ of an oligonucleotide duplex may be experimentally determined or predicted using the following formula $T_m = 81.5 + 16.6(\log_{10}[Na^+]) + 0.41$ (fraction G+C)$-(60/N)$, where N is the chain length and $[Na^+]$ is less than 1 M. See Sambrook and Russell (2001; Molecular Cloning: A Laboratory Manual, 3$^{rd}$ ed., Cold Spring Harbor Press, Cold Spring Harbor N.Y., ch. 10). Other more advanced models that depend on various parameters may also be used to predict $T_m$ of oligonucleotide duplexes may also be used depending on various hybridization conditions.

As used herein, the term "$T_m$-matched" refers to a plurality of nucleic acid duplexes having $T_m$s that are within a defined range, e.g. ±5° C., ±10° C., or ±15° C.

The term "hybridization conditions" as used herein refers to hybridization conditions that are sufficient to anneal an oligonucleotide of a sufficient length to a probe that is complementary to a nucleotide sequence of the probe. The hybridization conditions provide for dissociation of duplexes that anneal over a short length of region (e.g. less than 50, less than 40, less than 30, or less than 20 contiguous nucleotides). Such conditions may differ from one experiment to the next depending on the length and the nucleotide content of the complementary region. In certain cases, the temperature for low-stringency hybridization may be 5°-10° C. lower than the calculated Tm of the resulting duplex under the conditions used.

The term "stringent assay conditions" as used herein refers to conditions that are compatible to produce binding pairs of nucleic acids, e.g., probes and targets, of sufficient complementarity to provide for the desired level of specificity in the assay while being incompatible to the formation of binding pairs between binding members of insufficient complementarity to provide for the desired specificity. The term stringent assay conditions refers to the combination of hybridization and wash conditions.

The term "mixture", as used herein, refers to a heterogeneous combination of elements, that are interspersed and not in any particular order. A mixture is heterogeneous and not spatially separable into its different constituents. Examples of mixtures of elements include a number of different elements that are dissolved in the same aqueous solution, or a number of different elements attached to a solid support at random or in no particular order in which the different elements are not spatially distinct. In other words, a mixture is not addressable. To be specific, an array of surface-bound oligonucleotides, as is commonly known in the art and described below, is not a mixture of surface-bound oligonucleotides because the species of surface-bound oligonucleotides are spatially distinct and the array is addressable.

As used herein, the term "data" refers to refers to a collection of organized information, generally derived from results of experiments in lab or in silico, other data available to one of skilled in the art, or a set of premises. Data may be in the form of numbers, words, annotations, or images, as measurements or observations of a set of variables. Data can be stored in various forms of electronic media as well as obtained from auxiliary databases.

If a nucleic acid probe "corresponds to" or is "for" a certain RNA, the nucleic acid probe base pairs with, i.e., specifically hybridizes to, that RNA. As will be discussed in greater detail below, a nucleic acid probe for a particular RNA and the particular RNA, or complement thereof, contains at least one region of contiguous nucleotides that is identical in sequence.

As used herein, the term "total cellular RNA" is an RNA sample that contains at least tRNA, rRNA, mRNA, lincRNA and small RNA.

As used herein, the term "depleted", in the context of a total cellular RNA sample that has been depleted for tRNA, rRNA, or another type of RNA, is total cellular RNA sample from which tRNA, rRNA, or another type of RNA has been subtracted, i.e., removed. Depletion may be done by subtraction (i.e., by removing RNAs hybridization), enzymatically (e.g., using RNAseH) or by blocking (e.g., by blocking the action of an enzyme such as reverse transcriptase by annealing an oligo in its path to block it).

As used herein, the term "initial RNA sample" is an RNA sample that has not been exposed to fragmentation conditions and that contains intact RNA molecules. Such a sample may contain, for example, total cellular RNA or a total cellular RNA that has been depleted for rRNA and/or tRNA, or another type of RNA. An initial RNA sample contains at least one type of intact long RNA and one type of short RNA.

As used herein, the term "fragmented RNA sample" is a sample that contains fragments of RNA. A fragmented RNA sample can made from an initial RNA sample by exposing the initial RNA sample to fragmentation conditions. Fragmented RNA samples include RNA that has been extracted from a formalin-fixed paraffin embedded tissue (FPET) sample.

As used herein, the term "long RNA molecules" refers to RNA molecules that are at least 50 nt in length. Long RNA molecules include mRNA molecules, rRNA molecules, tRNA molecules, pre-miRNAs, snRNAs and long non-coding RNA molecules such as large intergenic RNA (lincRNA) molecules. Some long RNA molecules may be in the range of 50 to 10 kb in length, e.g., 200 nt to 10 kb in length.

As used herein, the term "short RNA molecules" refers to RNA molecules that are below 50 nt in length. Short RNA molecules a variety of small non-coding regulatory RNAs generically referred herein to as "small RNAs", i.e, short interfering RNAs, microRNAs, tiny non-coding RNAs piwi-interacting small RNAs (piRNAs) and small modulatory RNAs.

As used herein, the term "fragments of long RNA molecules" refer to RNA fragments that are obtained by fragmentation of long RNA molecules. Depending on how fragmentation is done, fragments of long RNA molecules may have a 5'OH group and a 2',3' cyclic phosphate group at the 3' terminus.

As used herein, the term "fragmentation conditions" refer to an environment or an agent that induces non-sequence specific fragmentation of long RNA molecules. As will be described in greater detail below, when fragmenting a sample containing both long RNA molecules and short RNA molecules, the fragmentation conditions can be tailored to provide for fragmentation of long RNA molecules without significant fragmentation of short RNA molecules.

As used herein, the term "adaptor" refers to an oligonucleotide that may be composed of any type of nucleotide. An adaptor may be, e.g., an RNA adaptor, a DNA adaptor, or it may be composed of both ribonucleotides and deoxyribonucleotides or analogs thereof. An adaptor may be labeled or unlabeled and in certain cases may be of 5-50 bases, e.g., 6 to 12 bases, in length or longer depending on the application.

As used herein, the term "blocked", when used in reference to an end of a nucleic acid that is blocked, e.g., a blocked 5' end or a blocked 3' end, is intended to refer to an end that is are not used as a substrate by the enzyme being used, e.g., the ligase being used. In certain embodiments, an end may be blocked using a dideoxy nucleotide, although many alternatives are known.

As used herein, the terms "5'-OH" and "5'-hydroxyl" refers to a nucleotide at the 5' terminus of a nucleic acid, where the nucleotide has a hydroxyl group at the 5' position.

As used herein, the terms "3'-OH" and "3'-hydroxyl" refers to a nucleotide at the 3' terminus of a nucleic acid, where the nucleotide has a hydroxyl group at the 3' position.

As used herein, the term "3'-P" or "3'-phosphate" refers to a nucleotide at the 3' terminus of a nucleic acid, where the nucleotide has a phosphate group at the 3' position.

As used herein, the term "5'-P" or "5'-phosphate" refers to a nucleotide at the 5' terminus of a nucleic acid, where the nucleotide has a phosphate group at the 5' position.

As used herein, the terms "2'-OH and 3'-PO" and "2'-hydroxyl and 3'-phosphate", in the context of a 3' terminus, refers to a nucleotide at the 3' terminus of a nucleic acid, where the sugar moiety of the nucleotide has both a phosphate group at the 3' position and a hydroxyl group at the 2' position.

As used herein, the term "2',3'-cyclic phosphate", in the context of a 3' terminus comprising 2',3'-cyclic phosphate, refers to a nucleotide at the 3' terminus of a nucleic acid, where the sugar moiety of the nucleotide has a phosphate group connected to the 2' and 3' positions, as shown below:

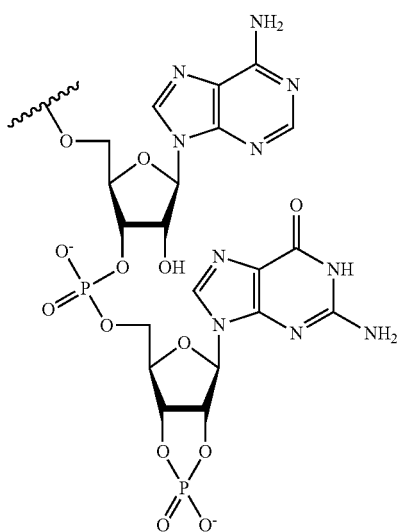

As used herein, the term "RtcB ligase" refers to any enzyme that has the ability to catalyze the ligation of the 3' end of an RNA having a 3' terminal 2'3'-cyclic phosphate to the 5' end of an RNA having a 5'-hydroxyl. Several examples of such enzymes (which are generically but not always referred to as "RtcB" protein in the art), are known in bacteria, archaea and eukarya (particularly in metazoan and protozoa species but not in some fungi and plants). RtcB ligases are structurally unrelated to 3'-OH RNA ligases, which ligate a 5'-phosphate-containing RNA to a 3'-hydroxyl-containing RNA, rather than ligating a 5'-hydroxyl-containing RNA to a 3' terminal 2',3'-cyclic phosphate-containing RNA. The structure, function, biochemical features and phylogenetic distribution of various RtcB ligases are described in a variety of publications, including: Tanaka et al (*RtcB is the RNA ligase component of an Escherichia coli RNA repair operon*. J. Biol. Chem. Jan. 11, 2011, e-pub ahead of print), Englert et al (*Archaeal 3'-phosphate RNA splicing ligase characterization identifies the missing component in tRNA maturation*. Proc. Natl. Acad. Sci. 2011 108: 2-7), and Okada et al (*Crystal structure of an RtcB homolog protein (PH1602-extein protein) from Pyrococcus horikoshii reveals a novel fold*. Proteins 2006 63: 1084-6)

As used herein, the term "3'-OH RNA ligase" refers to an enzyme that catalyzes the ligation of the 3' end of an RNA containing a 3'-hydroxyl to the 5' end of an RNA containing a 5'-phosphate in an ATP-dependent reaction. Many examples of these enzymes are known. 3'-OH RNA ligases may be derived from bacteriophage, or from their prokaryotic hosts, for example. T4 RNA ligase is one example of a 3'-OH RNA ligase (see, e.g., Wood et al, Mol. Cell. 2004 13: 455-6), and others are known (e.g., Torchia et al (*Archaeal RNA ligase is a homodimeric protein that catalyzes intramolecular ligation of single-stranded RNA and DNA*. Nucl. Acids Res. 2008 36: 6218-6227).

DESCRIPTION OF EXEMPLARY EMBODIMENTS

Before the present invention is described in greater detail, it is to be understood that this invention is not limited to particular embodiments described, and as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Method of Sample Analysis

Certain embodiments of the method involve fragmenting an initial sample of RNA that contains intact long RNA and intact short RNA to obtain a fragmented RNA sample. The long RNA in the initial sample is at least 50 nucleotides in length and may include cellular mRNA, long non-coding RNAs (such as lincRNA) and/or tRNA and rRNA, for example. The defining characteristics of mRNA, rRNA and rRNA are well known. lincRNA is relatively newly discovered, and is believed to be involved in regulating wide variety of processes, e.g, embryonic stem cell pluripotency, cell proliferation, cancer and chromatin structure. This class of molecules is reviewed by Gingeras (Nature Biotechnology 2009 27: 346-347). The short RNA of less than 50 nucleotides in length in the initial sample include a variety of small non-coding regulatory RNAs generically referred herein to as "small RNAs", i.e, short interfering RNAs, microRNAs, tiny non-coding RNAs, piwi-interacting small RNAs (piRNAs) and small modulatory RNAs. Small RNAs are a group of non-coding regulatory RNAs that have defined sequences and that are in the range of 18-31 nucleotides (nts) in length. Many small RNAs are approximately 19-25 nts in length.

Small RNAs are generally reviewed in Novina et al (Nature 2004 430:161-164) and may be classified in at least five groups: a) short interfering RNAs (siRNAs), b) micro-RNAs (miRNAs), c) tiny non-coding RNAs (tncRNAs), d) piwi-interacting RNAs (piRNAs) and e) small modulator RNAs (smRNAs). siRNAs are a class of double stranded RNAs of approximately 21-22 nt in length, generated from double stranded RNAs. siRNAs are thought to silence gene expression by promoting the cleavage of mRNAs. miRNAs, on the other hand, are a class of single-stranded RNAs of approximately 19-25 nt in length. miRNAs appear to be evolutionary conserved and are thought to silence gene expression by inhibiting translation. tncRNAs are a class of RNAs that are about 20-22 nucleotides. tncRNAs appear to be developmentally regulated, although their function is unknown. smRNAs are double stranded RNAs involved in regulating neuron-specific gene expression in adult neurons. piRNA forms RNA-protein complexes through interactions with Piwi proteins.

miRNAs are of particular interest. The sequences of several hundred miRNAs from a variety of different species, including humans, may be found at the microRNA registry (Griffiths-Jones, Nucl. Acids Res. 2004 32:D109-D111), and at the miRBase hosted by the Faculty of Life science at the University of Manchester (UK). The sequences of all of the microRNAs deposited at the microRNA registry, including 227 microRNA sequences from humans (see Lagos-Quintana et al, Science 294:853-858 (2001); Grad et al, Mol. Cell. 11:1253-1263 (2003); Mourelatos et al, Genes Dev 16:720-728 (2002); Lagos-Quintana et al, Curr. Biol. 12:735-739 (2002); Lagos-Quintana et al, RNA 9:175-179 (2003); Dostie et al, RNA 9:180-186 (2003); Lim et al, Science 299:1540 (2003); Houbaviy et al, Dev. Cell 5:351-358 (2003); Michael et al, Mol. Cancer. Res. 1:882-891 (2003); Kim et al, Proc. Natl. Acad. Sci. USA 101:360-365 (2004); Suh et al, Dev. Biol 270:488-498 (2004); Kasashima et al, Biochem. Biophys. Res. Commun. 322:403-410 (2004); and Xie et al, Nature 434:338-345 (2005)), are incorporated herein by reference. The methods and compositions described above and below may be used, for example, to analyze any of the microRNAs deposited at the microRNA registry, as well as others. As will be described in greater detail below, certain embodiments of the method described herein are particularly useful for the analysis of small RNAs of 18-31 nucleotides.

In certain embodiments, the method may comprise obtaining a RNA sample comprising: i. RNA fragments of long RNA molecules, wherein the fragments comprise a 5'-OH group and a 2',3'-cyclic phosphate group; and ii. unfragmented short RNA molecules that comprise a 5' OH group and a 3' OH group. Short RNA molecules naturally exist in the cell as molecules that contain a 5' phosphate group and a 3' OH group. As such, prior to starting the method, an initial (unfragmented) heterogeneous RNA sample may be treated with a phosphatase (e.g., calf intestinal phosphatase (CIP), shrimp alkaline phosphatase (SAP) or Antarctic phosphatase (AAP)) in order to provide short RNA molecules that comprise a 5' OH group and a 3' OH group; long RNA molecules such as messenger RNAs contain a 7-methylguanosine moiety at their 5' terminus, and are not substrates for the phosphatases mentioned above. After dephosphorylation of the small RNAs and inactivation of the phosphatase, either by heat-inactivation or by other methods, the long RNA molecules, are fragmented to produce numerous shorter RNA fragments containing a 5'-OH group and a 3' terminus having a 2',3'-cyclic phosphate group, without any further enzymatic treatment.

In general terms, a fragmented RNA sample may be made by exposing an initial RNA sample comprising intact long RNA molecules and short RNA molecules to fragmentation conditions that favor (e.g., maximize) fragmentation of the long RNA molecules relative to fragmentation of the short RNAs molecules. The fragments produced by this method may contain a 5'-OH and a 3' terminus having a 2',3'-cyclic phosphate group or a 2'-hydroxyl and 3'-phosphate. While there are other ways of producing such fragments, one embodiment involves exposing an initial RNA sample (which may contain, for example, total cellular RNA, total RNA that has been depleted for one or more types of RNA (e.g., rRNA and/or tRNA), or mRNA and small RNA, long non-coding RNA and small RNA, for example, although other combinations are contemplated) to a metal ion at a temperature of at least 50° C. for a suitable period of time.

Methods for fragmenting RNA to produce fragments that contain 5'-OH group and a 3' terminus having a 2',3'-cyclic phosphate group include chemical, enzymatic or thermal fragmentation methods, protocols for which are known (see, e.g., Chandler et al, Appl. Environ. Microbiol. 2003 69:2950-2958, Guschin et al Appl. Environ. Microbiol. 1997 63:2397-2402; Kelly et al, Anal. Biochem. 2002 311:103-118, Liu et al Environ. Microbiol. 2001 3:619-629, Mehlmann et al, Anal. Biochem. 2005 347:316-323, Nguyen Nucleic Acids Res. 2000 28:3904-3909, Proudnikov Nucleic Acids Res. 2006 24:4535-4542, Small et al, Appl. Environ. Microbiol. 2001 67:4708-4716). In one embodiment, the intact RNA may be fragmented using alkali by, e.g., incubation in NaOH (e.g., 50 mM NaOH) at an elevated temperature (e.g., 55° C.) for a period of time (e.g., 10-30 minutes), as described in Liu et al (Applied and Environmental Microbiology, 2007 73: 73-82). In other embodiments, the fragmentation may be metal ion catalyzed in that the intact RNA may be incubated with a metal ion, e.g., an ion of the lanthanide series or a divalent metal ion such as $Mg^{2+}$ or $Zn^{2+}$ (which may be at a concentration of, e.g., 5 mM to 200 mM) at an elevated temperature (e.g., in the range of 50° C. to 95° C.) for a period of time e.g., 1 minute to 1 hr, as described in, e.g., Brown et al (J. Am. Chem. Soc. 2002 124: 7950-7962). For example, RNA may be fragmented by incubation with 10 mM of zinc sulfate ($ZnSO_4$) or zinc chloride ($ZnCl_2$) in 25 mM of Tris-HCl (pH 7.4) at 60° C. for 30 min, as described by Liu, supra. In another case, the RNA may be incubated with 10 mM $ZnCl_2$ in 10 mM Tris-HCl pH 7 for 15 minutes at 70° C. to produce fragments of 60 to 200 bases in length. Incubation of RNA in 40 mM Tris-acetate pH 8.1, 100 mM KOAc and 30 mM MgOA for 20-30 min at 75° C. results in fragments that are generally between 38 and 150 bases in length, as described by Mehlmann et al (Analytical Biochemistry 2005 347: 316-323). In alternative embodiments, RNA fragments containing a 2'-hydroxyl and 3'-phosphate may be made using a ribonuclease, e.g., ribounclease T2. All of the incubation periods described above may be altered to increase or decrease the lengths of the fragments that are obtained, as desired. The fragmented sample may contain RNA fragments that are, on average, of a length in the range of 30 to 300 nucleotides in length, e.g., 50 to 200 nucleotides in length, in certain cases up to 500 nucleotides in length. The ability to fragment RNA to a desired length, coupled with the methods described below, allows one to analyze (e.g., select or sequence of, etc.) fragments of a particular size range.

Since fragmentation using the above methods occurs non-specifically at approximately random positions throughout the RNA, the fragmentation on average occurs in longer RNAs on a per molecule basis because the longer RNA molecules contain more potential sites for fragmentation to occur. For example, fragmentation conditions that fragment RNA to fragments of 60 to 200 bases in length should, on average, fragment an RNA molecule of 3 kb in length at approximately 15 to 50 sites without fragmenting a small RNA of approximately 18-31 nucleotides in length. Fragmentation of an RNA sample that contains long RNA molecules and short RNA molecules therefore results in a fragmented sample that contains: a) fragments of long RNA molecules and b) short RNA molecules which are largely intact. The short RNA molecules in the fragmented sample have defined ends in that the nucleotide sequences at the ends of the molecules might be known, whereas the fragments of long RNA (because cleavage is not sequence specific) do not have defined ends. The short RNA molecules are generally unfragmented. As shown in FIG. 1, fragmentation of long RNAs also results in 5' end fragments that may contain a 7 mG(5')ppp(5') cap structure. If these 5' fragments are to be analyzed using the subject method, the cap can be removed using a pyrophosphatase such as tobacco acid pyrophosphatase (TAP) or another similar enzyme. Likewise, the 3'-terminal (i.e. the downstream-most) fragment of fragmented long RNAs will contain hydroxyl groups at both the 3' and 5' ends. These fragments can be processed and analyzed using the same method as that used for analysis of the small RNA molecules (which will also contain hydroxyl groups at both 3' and 5' ends after an initial phosphatase treatment), as described below.

The enzyme used in the method (i.e., the RtcB ligase) may be derived from a variety of species, including archaeal, bacterial and eukaryotic species. Exemplary archaeal species from which the enzyme may be obtained include, for example: *M. kandleri, M. thermautotrophicus, M. smithii, M. stadtmanae, M. jannashi, M. aeolicus, M. maripaludis, M. vannieli, A. fulgidus, M. labreanum, M. boonei, M. hungatei, M. marsngiri, M. palustris, M. thermophila, M. burtonii, M. barkeri, M. mazei, M. acetivorans, P. furiosus, P. abyssi, P. horikoshii, T. sibiricus, T. kodakarensis, T. gammatolerans, T. onnurineus, T. pendens, C. maquilingensis, P. calidifontis, P. arsenaticum, P. aerophilum, T. neutrophilus, P. islandicum, D. kamchatkensis, S. marinus, S. acidocaldarius, S. tokodaii, S. islandicus, M. sedula, S. solfataricus, I. hospitalus, A. pernix, H. butylicus, H. borinquense, H. turkenica, N. magadii, H. utahenis, N. pharaonis,* H. sp NRC-1, *H. lacusprofundi, N. equitans, T. acidophilum, T. volcanium, F. acidomarnus* and *P. torridus.* Sequences for these proteins have been deposited into NCBI's Genbank database by others.

Exemplary bacterial species from which the enzyme may be obtained include, for example: *D. radiodurans, C. aurantiacus,* P. sp JDR-2, *B. halodurans, M. xanthus, K. radiotolerans, A. aurescens, R. erythropolis, C. aurimucosum, S. cellulosum, M. xanthus, T. turnerae, D. dadantiis,* E. sp 638, *S. enterica, E. coli, P. aeruginosa, C. violaceum, R. pickettii, C. taiwanensis, V. paradoxus, P. naphthalenivorans, D. acidovorans, B. avium, X. campestris, S. maltophilia, D. aromatica,* T. sp MZ1T, *S. viridis, A. baumannii,* A. sp BH72, *H. chejuensis, J. denitrificans, B. faecium, N. farcinica, S. viridis, T. fusca, S. avermitilis, C. acidiphila, S. ruber, A. mirum, F. alni, M. aeruginosa, A. marina, N. punctiforme, A. variabilis, C. thalassium, B. bacteriovorus, L. sphaericus, L. welshimeri, D. hafniense, C. thermocellum, A. oremlandll, N. europea, T. maritima, T. thermophilus, A. aeolicus* and *K. olearia.* Sequences for these proteins have been deposited into NCBI's Genbank database by others.

Exemplary eukaryotic species from which the enzyme may be obtained include, for example: *C. merolae, A. anophagefferens,* M. sp. RCC299, *O. lucimarinus, C. intstinalis, B. malayi, C. elegans, S. purpuratus, B. floridae, G. gallus, T. guttata, D. rerio, N. vectensis, D. discoideum, T. annulata, P. falciparum, D. palex, N. vitripennis, A. mellifera, T. castaneum, A. pisum, D. melanogaster, A. gambiae,* and *T. equinum* as well as mammal, e.g., *M. domestica, M. mulatta, S. scrofu, E. caballus, R. norvegicus, O. anatinus, B. tarus, C. lupus, P. troglodytes* and *H. sapiens.* Sequences for these proteins have been deposited into NCBI's Genbank database by others.

Further sequences may be identified by performing sequence comparisons, e.g., by BLAST searches, any of the sequences listed above with NCBI's sequence database. The method may be performed using as yet underscovered orthologs of RtcB. Other wild type sequences can be obtained by routine methods (e.g., by PCR or by hybridization, etc.).

The structure/function relationships of the *E. coli* RtcB is described in Tanaka, (supra) and the *P. aerophilum* RtcB is described in Englert (supra). The ligase activity of recombinant *E. coli* RtcB is manganese II-dependent, whereas recombinant *P. aerophilum* RtcB is metal ion ($Zn^{2+}$) dependent, and mutagenesis of that protein implicated Cys100, His205, and His236 as residues that are at the active site. This work is an agreement with the crystal structure of the *P. horikoshii* protein (Okada, supra).

In bacteria, it is thought that group I introns (which exist in pre-tRNAs) self-splice, resulting in the ligation of exons together to form the mature tRNA molecules. As such, it is possible that RtcB does not function in the splicing of tRNAs molecules in some species. In the *E. coli* genome and in the genomes of many other species, rtcB is in an operon with two other genes, rtcA and rtcR. RtcR is a transcriptional regulator and regulates the expression of rtcA and rtcB. RtcA is found in bacteria, archaea, and eukaryotes including humans (see, e.g., Genschik et al (J. Biol. Chem. 1998 273:25516-25526), Genschik et al (EMBO J. 1997 16:2955-2967) and Tanaka et al (RNA 2009 15:1865-1874)). RtcA is an RNA 3'-terminal phosphate cyclase that converts a 3'-phosphate at the end of an RNA molecule to a 2',3'-cyclic phosphodiester. The 2',3'-cyclic phosphodiester is a substrate of RtcB. We had anticipated that 3'-P would not be a substrate for RtcB, but we have determined that recombinant *A. fulgidis* RtcB can utilize either 3'P or 2',3'-cyclic phosphate as a splicing substrate in vitro. A phylogenetic analysis by Englert, supra, suggests that the last common ancestor of archaea and eukaryotes possessed an RtcB that functioned similarly to the *P. aerophilum* RtcB, and the conservation of RtcB implicates it as a eukaryotic 2',3'-cyclic phosphate RNA ligase. RtcB is absent in *Saccharomyces cerevisiae* and some plants, although yeast and plants have a structurally different RNA ligase that works through a distinct mechanism; there are no known orthologs of RtcB in these organisms. Interestingly, deletion of *S. cerevisiae* TRL1 (the tRNA ligase that normally functions to repair broken tRNAs in this organism) is lethal, but this phenotype can be rescued by complementation with *E. coli* RtcB, suggesting that although *S. cerevisiae* TRL1 and RtcB enzymes are not orthologs, they evolved convergently to catalyze similar RNA repair reactions.

Given that the amino acid sequences for the same enzyme from several different species are known, the crystal structure of one protein is known, the active site is known at least two proteins have been characterized biochemically and activity assays are known, variants of a wild type enzyme may be designed and used. In particular embodiments, the enzyme used in the method may be naturally occurring (i.e., found in nature) or may be non-naturally occurring. Non-naturally occurring enzymes may have an amino acid sequence that is at least 50%, e.g., at least 60%, at least 70%, at least 80%, at least 90%, at least 95%, at least 98%, or at least 99% identical to a wild type enzyme. For example, variants may be designed by aligning sequences from different species, and transferring amino acids residues that are at the same position (particularly conserved amino acids) but different from one sequence to another.

Also, as will be described below, in certain cases the enzyme used may be thermostable (i.e., capable of at least 50% of its original activity after heating to 70° C. for 10 minutes in its recommended reaction buffer) or heat sensitive (i.e., capable of less than 1% of its original activity after heating to 70° C. for 10 minutes in its recommended reaction buffer). Thermo stable enzymes may be obtained from thermostable species, e.g., in thermophilic archaea or thermophilic bacteria. For example, the genes of the Rtc operon are present in *Pyrococcus furiosis* (which has an optimal growth temperature of 100° C.), *Archaeoglobus fulgidis* (which has an optimal growth temperature of 83° C.), *Methanobacterium thermoautotrophicum* (which has an optimal growth temperature of 65-70° C.), and many other thermophilic archaea and bacteria, as described above. A 3'-OH RNA ligase that joins RNA fragments containing a 5'-PO and a 3'-OH has been identified in *Methanobacterium thermoautotrophicum* (MthRnl; Torchia et al, supra). These enzymes or their orthologs from other species may be employed in certain embodiments of the method.

As mentioned above, the adaptor used in the initial ligation step may in certain embodiments contain an affinity tag. In these embodiments, the method may further comprise separating the adaptor-ligated fragments of long RNA from the non-ligated short RNAs using the affinity tag. For example, if the affinity tag is biotin, the adaptor-ligated fragments of long RNA can be separated from the other RNA using streptavidin or avidin beads, methods for the use of which are well known in the art. This method provides an effective way for purifying sequences from long RNA away from short RNA sequences.

Certain aspects of one embodiment of the method may be described with reference to FIG. 1, which illustrates a way of making a sequencing library. The method may further include a purification step by which unligated adaptors are removed, e.g., by size exclusion or by affinity, or alternatively, by exploitation of enzymatic specificity. This step may be done at any logical point during the method.

In one embodiment, total RNA is isolated from source cells and is treated with a phosphatase that remove 5' phosphate groups from the small RNAs, which are referred to as "microRNAs" in FIG. 1 (step 1). In particular cases, particularly if the enzyme is to be heat-inactivated rather than inactivated by some other means (e.g., phenol/chloroform) this step may be done using Antarctic phosphatase (AAP) or another heat-inactivatable alkaline phosphatase. The phosphatase can be inactivated by heat-inactivation at 75° C. to 95° C. Although this step may be performed separately if a heat-stable phosphatase is used, during the heat-inactivation in step 2, the long RNA targets are fragmented into fragments containing 5'OH-nnn-2',3'-cyclic phosphate (i.e., "2',3'>P"). In step 3, a first adaptor that comprises a 5'-OH and a 3' dideoxy group is ligated to the sample using RtcB. RtcB ligates the adaptor to the 2',3'>P terminus of fragmented long RNAs to produce adaptor-ligated fragments of long RNA that comprise a 5'-OH and a 3'-dideoxy, as well as intact short RNAs that have not been ligated to this 5'OH-nmr-2',3'>P adaptor.

In certain embodiments and as illustrated, a molar excess of two different oligonucleotide adaptors may be ligated. These adaptors may have either identical or different nucleotide sequences, but will contain different 5' ends. The adaptor for long RNA fragments (i.e., the "first adaptor"; shown as OH-dd oligonucleotide in the table below and 5'OH~3' dd in FIG. 1) may contain a 5'-hydroxyl and a 2'-OH, 3'-dd. The adaptor for short RNA molecules (i.e., the "second adaptor"; shown as P-dd oligo in the table below and 5'P~3' dd in FIG. 1) on the other hand contains a 5'-P and a 3'-dideoxy. The second adaptor may be ligated to the short RNAs using a 3'-OH RNA ligase (shown as Rnl in FIG. 1). In this embodiment, RtcB ligates that first adaptor to the long RNA fragments to produce adaptor-ligated fragments of long RNA that comprise a 5'-OH and a 3'-dideoxy, and the 3'-OH ligase such as for example Rnl ligates the second adaptor to the 3' end of the short RNA molecules, thereby producing a ligated RNA sample comprising, in addition to the adaptor-ligated fragments of long RNA (which contain a 5'-OH and a 3'-dideoxy), adaptor-ligated short RNA molecules that also comprise a 5'-OH and a 3'-dideoxy. In particular cases, a heat stable enzyme may be employed for one or both ligation steps. For example, MthRNL (a 3'-OH ligase) can be employed to ligate the appropriate adaptor to the 3' terminus of the short RNAs, and an archaeal RtcB ligase can be employed to ligate the appropriate adaptor to the 2',3'>P terminus of fragmented long RNAs. Such enzymes can be used at a relatively high temperature (e.g., somewhere in the range of 65°-75°). At this higher temperature, all RNAs in the sample should have relaxed secondary structure and each RNA will receive exactly one adaptor at its 3' terminus. Because of the design of the adaptors and the enzymes used, no ligation to the 5' end of the fragmented RNA or the short RNA can occur.

As noted above, in certain embodiments, the sequence of the adaptor may be compatible with the primers used in a next generation sequencing platform (which will be described in greater detail below). As such, in some embodiments, the nucleotide sequence of the adaptor oligonucleotide may be complementary to or the same as one of the amplification primers used in a chosen sequencing platform.

As noted above, the ligated sample can be size-fractionated by passage through a spin-column (such as a G50 sephadex column or a Qiaquick column), whereby unligated adaptor oligos are removed. This purification step can be performed at any logical point during the method.

After the initial ligation, the ligated sample may be further processed by a variety of different methods. For example, in the embodiment shown in FIG. 1, the ligated RNA sample may be contacted with a third adaptor comprising a blocked 5' end (i.e., 5' end that is not recognized by the enzyme used, e.g., a '5'phosphate) and a 3' end having a 2'-OH, 3'-phosphate or 2',3'-cyclic phosphate in the presence of an RtcB ligase. This ligation of this 3'-terminal phosphate-containing adaptor to the ligated RNA sample produces two populations of RNAs that contain a common third adaptor at the 5' end, and respectively either the first adaptor or second adaptor at the 3' end. The first and second adaptors ligated to the 3' end may or may not have the same nucleotide sequence. In this embodiment, the two populations of RNAs may be reverse transcribed using a primer extension primer that binds to the first or second adaptors to produce two populations of cDNA products, one being a representation of the long RNA population and the other one being a representation of the short RNA population. This step may be done in the same way as the reverse transcription step described below. In particular cases, the two cDNA populations can be both or individually clonally amplified using PCR primers that bind to the adaptors at the ends of the primer extension products, and sequenced. In other cases, the two cDNA populations or amplified versions thereof may be both or individually labeled and analyzed by other means, e.g., by hybridizing them to a microarray. In a particular embodiment, the first and second adaptors have different sequences, and the method further comprises amplifying either the adaptor-ligated fragments of long RNA or the adaptor-ligated short RNA using a first primer that is complementary to only one of said first and second adaptors or its complement and a second primer that is complementary to said third adaptor or its complement. Alternatively, the first and second adaptors have the same sequence, and the method further comprises amplifying both the adaptor-ligated fragments of long RNA and the adaptor-ligated short RNA using a first primer that is complementary to both of said first and second adaptors or their complement and a second primer that is complementary to said third adaptor or its complement.

In particular embodiments, these primer-extension oligonucleotides may be made of unstructured nucleic acid (UNA), i.e., may be a nucleic acid that contains one or more UNA nucleotides that bind to naturally occurring nucleotide with higher stability than it binds to other UNA nucleotides. Further description of UNAs is found in published U.S. patent applications 20030211474, 20040086880, and Kutyavin et al., (Nucl. Acids. Res. 2002 30:4952-4959) which are incorporated by reference in their entirety.

After primer-extension oligonucleotide annealing, which can recognize either or both populations of RNA (ie. fragemented RNAs or small RNAs), the annealed primer-extension oligonucleotide may be extended (step 6) by the addition of reverse transcriptase and dNTPs from the 3' adaptors, across the ligated RNA sequences, and into the upstream adaptors. In some cases, the cDNA products can be clonally amplified using PCR primers (step 7) that bind to the adaptors at the ends of the primer extension products, and sequenced. Again, in other cases, the cDNA products or amplified versions thereof may be labeled and analyzed by other means, e.g., by hybridizing them to an array.

The following table summarizes certain steps of the method:

| action | time (h) | comments |
| --- | --- | --- |
| add Antarctic phosphatase | 0.5 | removes 5'P from miRNAs |
| to total RNA heat to 85 C. | 0.5 | inactivates AAP, non-miRNAs are fragmented into < 500nt [5'-OHnnn2',3' > P] pieces |
| add P-dd oligo & MthRNL; add OH-dd oligo and RtcB | 0.5 | ligates adapter oligos to the 3' end of miR and fragmented RNAs, respectively |
| spin column | 0.1 | removes free adaptors |
| Add 5' adaptor and RtcB, heat to 65-75 C. | 0.5 | 5' adaptor ligation |
| add primer-extension oligo, RT | 0.5 | makes cDNA flanked by adaptors |
| PCR to amplify cDNA | 1.5 | linear amplification of library |
| total time elapsed | 4.1 | |

The cDNA products generated by this method will be compatible with one or more next-generation sequencing platforms. In certain embodiments, the products may be clonally amplified in vitro, e.g., using emulsion PCR or by bridge PCR, and then sequenced using, e.g., a reversible terminator method (Illumina and Helicos), by pyrosequencing (454) or by sequencing by ligation (SOLiD), or by sequencing with other emerging next-generation sequencing technologies (Ion Torrent, Nanopore sequencing, Pacific Biosciences SMRT sequencing, etc.). Examples of such methods are described in the following references: Margulies et al ("Genome sequencing in microfabricated high-density picoliter reactors". Nature 2005 437: 376-80); Ronaghi et al ("Real-time DNA sequencing using detection of pyrophosphate release". Analytical Biochemistry 1996 242: 84-9); Shendure ("Accurate multiplex polony sequencing of an evolved bacterial genome". Science 2005 309: 1728); Imelfort et al ("De novo sequencing of plant genomes using second-generation technologies". Brief Bioinform. 2009 10:609-18); Fox et al ("Applications of ultra-high-throughput sequencing". Methods Mol. Biol. 2009 553:79-108); Appleby et al ("New technologies for ultra-high throughput genotyping in plants". Methods Mol. Biol. 2009 513:19-39) and Morozova ("Applications of next-generation sequencing technologies in functional genomics". Genomics. 2008 92:255-64), which are incorporated by reference for the general descriptions of the methods and the particular steps of the methods, including all starting products, reagents, and final products for each of the steps.

In some embodiments, the RNA fragments of the long RNA molecules may comprise 2',3'-cyclic phosphate group or 2'-hydroxyl and 3'-phosphate. The 5' group of the long RNA fragments may vary and in certain cases may be a 5'-OH group. In some embodiments, the unfragmented short RNA molecules may comprise a 5' OH group. The 3' group of unfragmented short RNA molecules may vary and in certain cases may be a 3' OH group.

Separately or in combination with the above, the first adaptor may comprise a 5'-OH. The 3' end of the first adaptor may vary and in certain cases may be blocked, e.g., using a 3' dideoxy nucleotide.

Depending on the ends of the RNAs and the adaptors, the ligating step may produce a ligated RNA sample comprising adaptor-ligated fragments of long RNA that comprise, for example, a 5'-OH-end. The 3' end of the ligated long RNAs may be blocked, e.g., using a dideoxy. The non-ligated short RNAs may comprise 5'OH and a 3'OH.

Kits

Also provided by the subject invention are kits for practicing the subject methods, as described above. The subject kits contain at least: a) a RtcB ligase which may in certain cases be thermostable; b) a phosphatase that removes the 5'-phosphate of a nucleic acid; and c) an adaptor that comprises a 5'-OH and a blocked 3' end (e.g., a dideoxy group). The kit may optionally contain other components, for example: reagents for fragmenting an RNA sample, a second adaptor that comprises a 5'-phosphate and a blocked 3' end, a third adaptor that contains a 5'-phosphate and either a 2'OH,3' phosphate or a 2',3'-cyclic phosphate, a 3'-OH RNA ligase (which may also be thermostable) and/or a reverse transcriptase, etc. The various components of the kit may be present in separate containers or certain compatible components may be precombined into a single container, as desired. Reagents for depleting or hybridization-based masking of certain RNAs from a sample (e.g., tRNA or rRNA) may also be present in the kit.

In some embodiments, the kit may further comprise reagents for fragmenting an RNA sample. In some embodiments, the kit may further comprise a second adaptor that comprises a 5'-phosphate and a 3'-phosphate. In some embodiments, the kit may further comprise a 3'-OH thermostable RNA ligase. In some embodiments, the kit may further comprise comprising a reverse transcriptase.

In addition to above-mentioned components, the subject kits may further include instructions for using the components of the kit to practice the subject methods, i.e., to instructions for sample analysis. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, this means for obtaining the instructions is recorded on a suitable substrate.

Utility

The methods described above may be employed to investigate the transcriptome of any organism, e.g., a plant (monocot or dicot), an animal such a vertebrate, e.g., a mammal (human, mouse, rat, etc), amphibian, reptile, fish, birds or invertebrate (such as an insect), or a microorganism such as a bacterium or yeast, etc.

The subject method may be employed in a variety of diagnostic, drug discovery, and research applications that include, but are not limited to: high throughput sequencing, genotyping, mutation detection, functional genomics, mapping and gene expression analysis. In particular embodiments, the method may be employed in the diagnosis or monitoring of a disease or condition (where the expression of short and/or long RNAs provide a marker for the disease or condition), discovery of drug targets (where a short and/or long RNA is differentially expressed in a disease or condition and may be targeted for drug therapy), drug screening (where the effects of a drug are monitored by assessing the level of a short and/or long RNA), determining drug susceptibility (where drug susceptibility is associated with a particular profile of a short and/or long RNA), basic research (where is it desirable to identify the presence and/or function of short and/or long RNAs in a sample, or, in certain embodiments, the relative levels of a particular short and/or long RNAs in two or more samples) and mutation detection, etc.

In certain embodiments, relative levels of small short and/or long RNAs in two or more different small RNA samples may be obtained using the above methods, and compared. In these embodiments, the results obtained from the above-described methods are usually normalized to the total amount of RNA in the sample or to control RNAs (e.g., constitutive RNAs), and compared. This may be done by comparing ratios, or by any other means. In particular embodiments, the short and/or long RNA profiles of two or more different samples may be compared to identify short and/or long RNAs that are associated with a particular disease or condition (e.g., a short and/or long RNA that is induced by the disease or condition and therefore may be part of a signal transduction pathway implicated in that disease or condition).

The different samples may consist of an "experimental" sample, i.e., a sample of interest, and a "control" sample to which the experimental sample may be compared. In many embodiments, the different samples are pairs of cell types or fractions thereof, one cell type being a cell type of interest, e.g., an abnormal cell, and the other a control, e.g., normal, cell. If two fractions of cells are compared, the fractions are usually the same fraction from each of the two cells. In certain embodiments, however, two fractions of the same cell may be compared. Exemplary cell type pairs include, for example, cells isolated from a tissue biopsy (e.g., from a tissue having a disease such as colon, breast, prostate, lung, skin cancer, or infected with a pathogen etc.) and normal cells from the same tissue, usually from the same patient; cells grown in tissue culture that are immortal (e.g., cells with a proliferative mutation or an immortalizing transgene), infected with a pathogen, or treated (e.g., with environmental or chemical agents such as peptides, hormones, altered temperature, growth condition, physical stress, cellular transformation, etc.), and a normal cell (e.g., a cell that is otherwise identical to the experimental cell except that it is not immortal, infected, or treated, etc.); a cell isolated from a mammal with a cancer, a disease, a geriatric mammal, or a mammal exposed to a condition, and a cell from a mammal of the same species, preferably from the same family, that is healthy or young; and differentiated cells and non-differentiated cells from the same mammal (e.g., one cell being the progenitor of the other in a mammal, for example). In one embodiment, cells of different types, e.g., neuronal and non-neuronal cells, or cells of different status (e.g., before and after a stimulus on the cells) may be employed. In another embodiment of the invention, the experimental material is cells susceptible to infection by a pathogen such as a virus, e.g., human immunodeficiency virus (HIV), etc., and the control material is cells resistant to infection by the pathogen. In another embodiment of the invention, the sample pair is represented by undifferentiated cells, e.g., stem cells, and differentiated cells. Two different developmental stages, e.g., embryo vs. non-embryo or young cells vs. old cells may also be compared.

Cells from yeast, plants and animals, such as fish, birds, reptiles, amphibians and mammals may be used in the subject methods. In certain embodiments, mammalian cells, i.e., cells from mice, rabbits, primates, or humans, or cultured derivatives thereof, may be used. Accordingly, among other things, the instant methods may be used to link the expression of certain genes to certain physiological events.

The invention claimed is:

1. A method of processing a heterogeneous RNA sample comprising:
   a) obtaining a fragmented RNA sample comprising:
      i. RNA fragments of long RNA molecules; and
      ii. unfragmented short RNA molecules; and
   b) contacting said fragmented RNA sample with a first adaptor in the presence of a RtcB ligase, thereby producing a ligated RNA sample comprising adaptor-ligated fragments of long RNA and unligated short RNAs.

2. The method of claim 1, wherein said fragmented RNA sample is made by exposing an initial RNA sample comprising intact long RNA molecules and unfragmented short RNA molecules to fragmentation conditions that favor fragmentation of said long RNA molecules relative to said short RNAs molecules.

3. The method of claim 2, wherein said exposing comprises contacting said initial RNA sample with a divalent cation at a temperature of at least 50° C.

4. The method of claim 1, wherein said unfragmented short RNA molecules are processed by contacting an initial RNA sample comprising small RNA molecules having a 5'-phosphate and a 3'-OH with a phosphatase that removes said 5'-phosphate from said short RNA molecules.

5. The method of claim 1, wherein said adaptor comprises an affinity tag, and the method further comprises separating said adaptor-ligated fragments of long RNA from said non-ligated short RNAs using said affinity tag.

6. The method of claim 1, wherein method further comprises contacting said fragmented RNA sample with a second adaptor comprising a 5'-phosphate and an unligatable 3'-dideoxy in the presence of a 3'-OH RNA ligase, thereby producing a ligated RNA sample comprising, in addition to said adaptor-ligated fragments of long RNA, adaptor-ligated short RNA molecules comprising a 5'-OH-end and a 3'-dideoxy-end.

7. The method of claim 1, wherein said first adaptor comprises a 5'-OH and a blocked 3' end.

8. The method of 6, wherein method further comprises contacting said ligated short and long RNA fragments with a third adaptor comprising a 5'-phosphate and a 3'-phosphate which may be in 2'OH,3'P or 2',3'-cyclic phosphate form, in the presence of a RtcB ligase, thereby producing a ligated RNA sample comprising adaptor-flanked long and short RNAs comprising a 5'-phosphate-end and a blocked 3'-end.

9. The method of claim 8, further comprising reverse-transcribing said RNA product using a primer that binds to the 5' ends of said first and second adaptors to produce a plurality of cDNA products.

10. The method of claim 9, wherein said primer comprises UNA nucleotides.

11. The method of claim 9, further comprising clonally amplifying and sequencing said cDNA products.

12. The method of claim 6, further comprising contacting said ligated RNA sample with a third adaptor comprising a blocked 5' end and a 2',3'-cyclic phosphate in the presence of an RtcB ligase, thereby producing a population of RNAs comprising said third adaptor at the 5' end, and either the first adaptor or second adaptor at the 3' end.

13. The method of claim 12, wherein said first and second adaptors have different sequences, and the method further comprises amplifying either the adaptor-ligated fragments of long RNA or the adaptor-ligated short RNA using a first primer that is complementary to only one of said first and second adaptors or its complement and a second primer that is complementary to said third adaptor or its complement.

14. The method of claim 12, wherein said first and second adaptors have the same sequence, and the method further comprises amplifying both the adaptor-ligated fragments of long RNA and the adaptor-ligated short RNA using a first primer that is complementary to both of said first and second adaptors or their complement and a second primer that is complementary to said third adaptor or its complement.

15. The method of claim 12, further comprising reverse transcribing said population of RNAs using a primer that binds to said first and second adaptors to produce a plurality of cDNA products.

16. The method of claim 15, further comprising clonally amplifying and sequencing said DNA products.

17. The method of claim 1, wherein said RtcB ligase is heat stable.

18. The method of claim 1, wherein said RtcB ligase has an amino acid sequence that is at least 90% identical to a wild-type RtcB ligase sequence.

19. The method of claim 15, wherein said wild-type RtcB ligase sequence is from a heat-tolerant archaebacterium.

* * * * *

UNITED STATES PATENT AND TRADEMARK OFFICE
CERTIFICATE OF CORRECTION

PATENT NO. : 9,074,203 B2  
APPLICATION NO. : 13/368600  
DATED : July 7, 2015  
INVENTOR(S) : Gusti Zeiner et al.

Page 1 of 2

It is certified that error appears in the above-identified patent and that said Letters Patent is hereby corrected as shown below:

On the Title page, in item (56), in column 2, under "Publications", line 5, delete "Eucarya," and insert -- Eukarya, --, therefor.

In the Drawings

On sheet 1, in Figure 1, line 5, Delete "inacitvate" and insert -- inactivate --, therefor.

In the Specification

In column 2, line 62, delete "e.g.:" and insert -- e.g.,: --, therefor.

In column 8, line 49, delete "is are" and insert -- is --, therefor.

In column 9, line 55, delete "1084-6)" and insert -- 1084-6). --, therefor.

In column 12, line 60, delete "ribounclease" and insert -- ribonuclease --, therefor.

In column 14, line 17, delete "underscovered" and insert -- undiscovered --, therefor.

In column 15, line 66, delete "5'OH-nmr-2',3'>P" and insert -- 5'OH-nnn-2',3'>P --, therefor.

In column 17, line 29-30, delete "fragemented" and insert -- fragmented --, therefor.

In column 18, line 3, delete "picoliter" and insert -- picolitre --, therefor.

Signed and Sealed this  
Twenty-second Day of March, 2016

Michelle K. Lee  
*Director of the United States Patent and Trademark Office*

In the Claims

In column 21, line 7, in claim 8, delete "method of" and insert -- method of claim --, therefor.

In column 21, line 13, Approximately, in claim 8, delete "3'-end." and insert -- 3' end. --, therefor.